United States Patent
Joshi et al.

(10) Patent No.: US 6,780,635 B2
(45) Date of Patent: Aug. 24, 2004

(54) PROCESS FOR THE PREPARATION OF OPTICALLY ACTIVE AZABICYCLO HEPTANONE DERIVATIVES

(75) Inventors: Rohini Ramesh Joshi, Maharashtra (IN); Asmita Ashutosh Prabhune, Maharashtra (IN); Ramesh Anna Joshi, Maharashtra (IN); Mukund Keshav Gurjar, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 178 days.

(21) Appl. No.: 10/033,197

(22) Filed: Dec. 27, 2001

(65) Prior Publication Data

US 2003/0143699 A1 Jul. 31, 2003

(51) Int. Cl.[7] ................................................ C12P 13/00
(52) U.S. Cl. ....................... 435/280; 435/128; 435/122; 435/136; 435/147; 435/227
(58) Field of Search .................. 435/280, 128, 435/122, 136, 147, 227

(56) References Cited

U.S. PATENT DOCUMENTS 6,340,587 B1 * 1/2002 Dawson et al. ............. 435/280

FOREIGN PATENT DOCUMENTS

| EP | 0 424 064 A1 | 4/1991 | |
|---|---|---|---|
| EP | 0 424 064 B1 | 4/1991 | C07D/209/52 |
| EP | 0 434 450 A3 | 6/1991 | C07D/473/00 |
| EP | 0 434 450 A2 | 6/1991 | C07D/473/00 |
| EP | 0 434 450 B1 | 7/1999 | C07D/473/00 |
| WO | WO 95/21161 | 8/1995 | C07D/239/48 |
| WO | WO 99/10519 | 3/1999 | |
| WO | WO 00/03032 | 1/2000 | C12P/41/00 |

OTHER PUBLICATIONS

Hiroto Nakano et al., *Tetrahedron Asymmetry*, 1996, 7:8, 2381–2386.
Mahmoud Mahmoudian et al., *Tetrahedron Asymmetry*, 1999, 10:1201–1206.
Stephen JC Taylor, *Bioorganic & Medicinal Chem.*, 1999, 7:2163–2168.
Susan Daluge et al., *J. Org. Chem.*, 1978, 43:12, 2311–2320.
Stephen JC Taylor, *Tetrahedron: Asymmetry*, 1993, 4:6, 1117–1128.
Stephen JC Taylor, *J. Chem Soc., Chem. Commun.*, 1990, 1120–1121.

* cited by examiner

*Primary Examiner*—Irene Marx
(74) *Attorney, Agent, or Firm*—Morgan & Finnegan, LLP

(57) ABSTRACT

The present invention provides a process for preparation of optically active azabicyclo heptanone derivates using lactamases that will react with racemic lactam of formula (I) to give a single enanotiomer of lactam (III) and the corresponding ring opened compound of formula (IV) in an enantiomerically pure form.

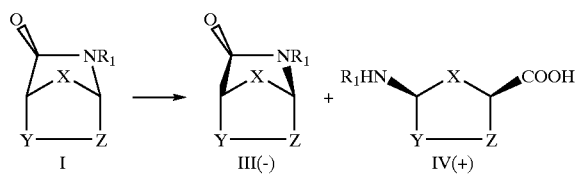

12 Claims, No Drawings

US 6,780,635 B2

PROCESS FOR THE PREPARATION OF OPTICALLY ACTIVE AZABICYCLO HEPTANONE DERIVATIVES

FIELD OF THE INVENTION

The present invention relates to a process for the preparation of an optically active azabicyclo heptanone derivative of general Formula III

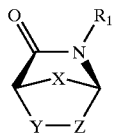

Formula III wherein $R_1$=H, X=$CH_2$, Y—Z=—CH=CH—, from a racemic mixture of the γ-lactams of Formula (I)

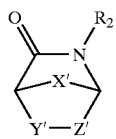

Formula I wherein $R_2$ is H or $COR_3$, ($R_3$ is $C_{1-4}$ alkyoxy, aryl or aryloxy),
X' is O or $CHR_4$ ($R_4$ is F, OH, Br, or H).
Y'—Z' is CH=CH,

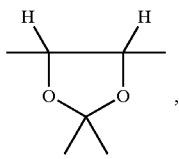

or —CH($R_6$)$CH_2$— ($R_6$=Br, OH, $PhCH_2O$, or $N_3$,

The present invention also relates to a process for the preparation of an optically active azabicyclo heptanone derivative of general Formula III wherein $R_1$=H, X'=$CH_2$, Y'—Z'=CH=$CH_2$ is useful as an intermediate in the synthesis of antiviral agents.

BACKGROUND OF THE INVENTION

Carbocyclic analogues of purines are known as antiviral and anti neoplastic agents. For example the compound of Formula II is described as having potent activity against human immunodeficiency virus (HIV) and Hepatitis B virus (HBV) (EP 0434450).

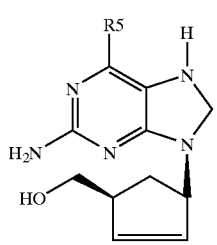

Formula-II wherein $R_5$=Cyclopropylamino, or N-Cyclopropyl, N-Methylarnine.

Prior art discloses the preparation of 9-substituted-2-amino purines starting from a pyrimidine compound, coupling with enantiomerically pure sugar/carbocyclic analogues residue and cyclization to form the imidazole ring followed by introduction of suitable 6-substituent (PCT/GB95/00225). Carbovir and known analogues are prepared from the known γ-lactam (Vince lactam) 2-azabicyclo[2,2,1]hept-5-en-3-one (Formula I) wherein X' is —$CH_2$, —Y'—Z'— is —CH=CH— and $R_2$ is H.

Prior art indicates that the final product or any intermediate or starting material may be resolved by known methods or the racemic mixture of the product may be enzymatically converted to chirally pure compound. The γ-lactam can be prepared by reacting cyclopentadiene with tosylcyanide, (Vince J. Org. Chem. 1978, 43, 2311).

There are several synthetic pathways where chemical resolution into the enantiomer has been effected but the enzymatic resolution of γ-lactam will be the most economical commercial process. γ-lactamase methodology has been reported based on enantio-complementary biotransformation. Enzymatic resolution of bicyclic lactam using whole cell cultures ENZA1 and ENZA2 has been reported to give both the optical forms of lactam (S. V. Teylor, J. C. S. Chem. Comm., 1121, 1990, Tet. Assy., 4, 1117–1128). The detailed process has been described in patent (EP 0424064). The racemic lactam was treated with ENZA-½ cell free extract at 30° C. with shaking for 14 days. The crude (+)/(−) lactam was isolated by extraction with dichloromethane and purified by column chromatography on silica gel to provide the (+) lactam with 88% optical purity, ee, and the (−) lactam with 98% ee, optical purity.

Enzymatic resolution of N-Acyl bicyclic lactam using acylase has been described in patent (PCT/EP99/04814) in 31% yield with 98% ee. The conversion of the optically active N-Acetyl-lactam to (+)/(−) lactam is tedious.

The prior art methods to the cyclopentane moiety of carbocyclic nucleosides starting from non-carbohydrate synthons or readily available meso compounds generally involve a number of steps, which are often difficult to perform and provide poor yields, making the practical scale-up of these processes difficult and uneconomical.

OBJECTS OF THE INVENTION

The main object of the present invention is to provide a process for the preparation of an optically active azabicyclo heptanone derivative which obviates the drawbacks of the prior art processes and use cheaper and easily available microbial whole cell enzyme.

It is another object of the invention to provide a process for the preparation of (−) 2-Azabicyclo[2,2,1]-hept-5-ene-3-one Formula III, which is economical and efficient.

SUMMARY OF THE INVENTION

The present invention provides a process for the preparation of optically active azabicyclo heptanone derivatives using lactamases that will react with racemic γ-lactam of Formula I to give a single enantiomer of lactam (III) and the corresponding ring opened compound of formula (IV) in an enantiomerically pure form.

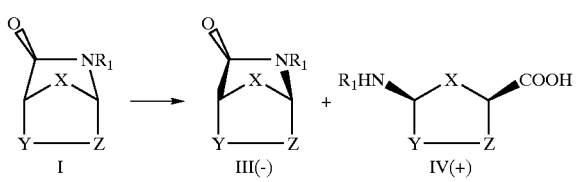

Accordingly, the present invention provides a process for the preparation of (−)2-Azabicyclo[2,2,1]-hept-5-ene-3-one Formula III wherein $R_1$=H, $X$=$CH_2$, Y—Z=—CH=CH—,

Formula III which comprises reacting a racemic mixture of a compound of Formula I:

Formula I wherein $R_2$ is H or $COR_3$, ($R_3$ is $C_{1-4}$ alkoxy, aryl or aryloxy), X' is O or $CHR_4$ ($R_4$ is F, OH, Br, or H), Y'—Z' is CH=CH,

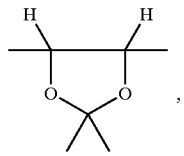

or —CH($R_6$)$CH_2$— ($R_6$=Br, OH, $PhCH_2O$, or $N_3$, with an enzyme, a lactamase or the whole cells of a microorgnism in a buffer containing organic solvent at temperature ranging between 25–30° C. for a period ranging from 14 to 24 hr., extracting the mixture into an organic solvent, separating the organic layer and removing the organic solvent to obtain the product.

In one embodiment of the invention the microorganisms or enzymes used are selected from Bacillus, Klyuvera or Eschericha.

In another embodiment of the invention the whole cell is obtained from growing a culture of *Klyuvera Citrophila*, ATCC No.21285 (*American Tissue and Type Culture, Box 1549, Manassas, Va. 20108*), in a conventional culture medium.

In another embodiment of the invention, the cell extract or enzyme used comprises an enzyme or a cell extract from Klyuvera sp. (ATCC No.21285).

In another embodiment of the invention the buffer used is selected from the group consisting of phosphate buffer (0.05 M–0.1 M, 6–8 pH), citrate buffer (0.05 M–0.1 M 6–7.5 pH) and Trisbuffer (0.05M–0.2M, 7–8 pH).

In another embodiment of the invention the buffer used comprises phosphate buffer (0.2 M, 7.4 pH).

In another embodiment of the invention the organic solvent used for the reaction along with buffer is selected from the group consisting of alcohols, alkyl acetates, ketones and sulfoxides.

In a further embodiment of the invention, the organic solvent is selected from the group consisting of methanol, ethanol, butanol, ethyl acetate, acetone, dimethyl sulfoxide and dimethylformamide.

In a further embodiment of the invention, the organic solvent comprises acetone.

In another embodiment of the invention the percent of organic solvent used for the reaction along with buffer is in the range of 5% to 50% (v/v).

In another embodiment of the invention the percent of organic solvent used for the reaction along with buffer comprises is 10%(v/v).

In another embodiment of the invention the solvent used for extraction comprises a chlorinated solvent selected from the group consisting of chloroform, ethylene dichloride, methylene dichloride and an alkyl acetate.

In another embodiment of the invention, the alkyl acetate used as the solvent for extraction comprises ethyl acetate.

In another embodiment of the invention the solvent used for extraction comprises methylene chloride.

In a feature of the invention the chemical yield (−) 2-Azabicyclo[2,2,1]-hept-5-ene-3-one is 39.3% and the optical purity is 98%.

DETAILED DESCRIPTION OF THE INVENTION

The process of the present invention is highly efficient with maximizes cost effectiveness by a fast resolution process to provide (−) lactam enantiomer, an important starting material for the production of the anti HIV agent (−) Carbovir and Abacavir.

The process of the present invention is described herein below with references to the following examples, which are illustrative only and should not be construed to limit the scope of the present invention in any manner.

EXAMPLE 1

This example describes general procedure for a biomass preparation using whole cell or an enzyme pre-inoculum (5–10 ml) prepared by growing a microorganism in a medium containing a yeast extract (0.5%), peptone (1%), sodium chloride (0.2%), sodium glutamate (0.5%) and phenyl acetic acid (15 mM) at pH 7.2–7.3 for 24 hr with shaking at 150 rpm. 300 ml of the above mentioned growth medium subsequently transferred to a 1 liter flask and incubated at 28–30° C. for 24 hours on a rotary shakers (150 rpm). The biomass of grown cells were separated by centrifuge and washed with phosphate buffer pH 6.8, The separated biomass or cell mass was used for the reaction described in Example 2.

EXAMPLE 2

The general procedure for the enantioselectsive hydrolysis of (±)-2-azabicyclo(2,2,1)hept-5-en-3-one, (Vince's lactam) (1) is as follows:

0.1 g (0.00092 mole parts) of (±)-2-azabicyclo[2,2,1]-hept-5-en-3-one (1) was suspended in phosphate buffer (5 parts) and 50 mg of the wet biomass of culture (ATCC No.21285) was added. The mixture was kept stirring for 72 hr. The cell mass was removed by filtering through celite and the filtrate was extracted with dichloromethane (5×10 parts). Removal of the solvent gave optically active Formula III in 31.8% chemical yield, and 58.2% ee.

EXAMPLE 3

The general procedure for the enantioselective hydrolysis of (±)-2-azabicyclo(2,2,1)hept-5-en-3-one, using the cell mass obtained from culture (ATCC No.21285) was followed. 0.1 g (0.00092 mole parts) of the (±) racemic mixture was suspended in phosphate buffer (5 parts) and an amount of the cell mass as indicated in Table 1 was added. The mixture was kept stirring for 24 hrs. The cell mass was then removed by filtering through celite and the filtrate was extracted with dichloromethane (5×10 parts). Removal of the solvent gave optically active Formula III. The results are summarized in Table 1.

TABLE 1

| Sr. No. | Cells Wet/Wt. % | Chemical Yield | Ratio R:S | ee % |
|---|---|---|---|---|
| 1. | 5 | 39.1 | 46.36:53.64 | 7.29 |
| 2. | 10 | 33.2 | 45.15:54.85 | 9.71 |
| 3. | 20 | 31.4 | 36.70:63.30 | 26.61 |
| 4. | 30 | 33.0 | 27.43:72.57 | 45.14 |
| 5. | 40 | 34.2 | 25.71:74.29 | 48.58 |
| 6. | 50 | 30.5 | 21.23:78.77 | 57.55 |

EXAMPLE 4

The general procedure for enantioselective hydrolysis of (±)2-azabicyclo(2,2,1)hept-5-en-3-one, using the cell mass from culture (ATCC No.21285) was followed. 0.2 g (0.00184 mole parts) of (±) was suspended in phosphate buffer and an organic solvent,(as indicated in Table 2) 10 parts. 0.1 gm of wet cell mass was added and kept stirring 24 hrs. The cell mass was removed by filtering through celite and the filtrate was extracted with dichloromethane (5×10 parts). Removal of the solvent gave optically active Formula III. The results are summarized in Table 2.

TABLE 2

| Sr. No. | Organic Solvent | Chemical Yield | Ratio R:S | ee % |
|---|---|---|---|---|
| 1. | Ethyl acetate | 27.1 | 13.39:86.61 | 73.22 |
| 2. | Methanol | 25.5 | 14.90:85.10 | 70.20 |
| 3. | Ethanol | 33.1 | 9.27:90.73 | 81.46 |
| 4. | Acetone | 44.2 | 9.69:90.31 | 80.62 |
| 5. | Dimethyl sulfoxide | 42.1 | 36.10:63.90 | 27.80 |

The ratio of phosphate buffer (0.2M, pH 7.4) to organic solvent is (9:1).

EXAMPLE 5

The general procedure for enantioselective hydrolysis of (±)2-azabicyclo(2,2,1)hept-5-en-3-one, using the cell mass from culture (ATCC No.21285) was followed. 0.2 g (0.00184 mole parts) of (±) was suspended in phosphate buffer and acetone (as indicated in Table 2) 10 parts. 0.1 gm of wet cell mass was added and the mixture was kept stirring for 24 hrs. The cell mass was removed by filtering through celite and the filtrate was extracted with dichloromethane (5×10 parts). Removal of the solvent gave optically active Formula III. The results of different proportions of acetone are summarized in Table 3.

TABLE 3

| Sr. No. | Buffer:Acetone (v/v) | Chemical Yield | Ratio R:S | ee % |
|---|---|---|---|---|
| 1. | 9.5:0.5 | 40.8 | 4.58:95.85 | 90.85 |
| 2. | 9.0:1.0 | 41.2 | 9.69:90.31 | 80.62 |
| 3. | 8.0:2.0 | 41.3 | 12.34:87.66 | 75.33 |
| 4. | 5.0:5.0 | Slow reaction | — | — |

EXAMPLE 6

The general procedure for the enantioselective hydrolysis of (±)2-azabicyclo(2,2,1)hept-5-en-3-one, using cell mass from culture (ATCC No.21285) was followed. 10.0 g (0.918 mole parts) of (±) was suspended in mixture of 475 parts of phosphate buffer and 25 parts of acetone in a 1 liter flask. Cell mass (wet. Weight~5 parts) was added and the reaction mixture was stirred at room temperature (28±1° C. After completion of the reaction (monitored by chiral HPLC) the reaction mixture was centrifuged in order to remove the cell mass. The supernatent liquid was extracted using a continuous extractor by dichloromethane. On evaporation of the solvent under reduced pressure, (1S, 4R) azabicyclo(2,2,1) hept-5-en-3-one III (3.93 gm) was obtained. Crystallization with a dichloromethane:ether mixture gave a product of 98% optical purity.

We claim:

1. A process for the preparation of optically active azabicyclo heptanone derivative of Formula III, wherein $R_1$=H, X=$CH_2$ Y—Z=—CH=CH—

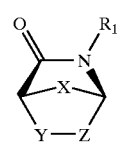

Formula III which comprises reacting a compound of formula I

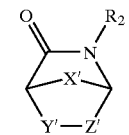

Formula I wherein $R_1$=—H, X'=—$CH_2$—, and Y'Z'=—CH=CH—, with an enzyme or whole cell or whole cell extract of *Klyuvera Citrophila* ATCC No. 21285 in a buffer containing organic solvent at temperature ranging between 25–30° C. for a period ranging from 10–24 hr., extracting the mixture with an organic solvent, separating the organic layer, and removing the organic solvent.

2. A process as claimed in claim 1 wherein the buffer used is selected from the group consisting of phosphate buffer at 0.05 M–0.1 M, pH 6–8; citrate buffer at 0.05 M–0.1 M, pH 6–7.5; and TRIS buffer at 0.05M–0.2Me, pH 7–8.

3. A process as claimed in claim 1 wherein the buffer used comprises phosphate buffer at 0.2 M, pH 7.4.

4. A process as claimed in claim 1 wherein the organic solvent used along with buffer is selected from the group consisting of alcohols, alkyl acetates, ketones and sulfoxides.

5. A process as claimed in claim 4 wherein the organic solvent is selected from the group consisting of methanol, ethanol, butanol, ethyl acetate, acetone, dimethyl sulfoxide and dimethyl formamide.

6. A process as claimed in claim 4 wherein the organic solvent comprises acetone.

7. A process as claimed in claim 1 wherein the percent of organic solvent used for the reaction along with buffer is in the range of 5% to 50%(v/v).

8. A process as claimed in claim 1 wherein the percent of organic solvent used for the reaction along with buffer comprises is 10%(v/v).

9. A process as claimed in claim 1 wherein the solvent used for extraction comprises a chlorinated solvent selected from the group consisting of chloroform, ethylene dichloride, methylene dichloride and an alkyl acetate.

10. A process as claimed in claim 9 wherein the alkyl acetate used for extraction comprises ethyl acetate.

11. A process as claimed in claim 9 wherein the solvent used for extraction comprises methylene chloride.

12. A process as claimed In claim 1 wherein the yield of (−) 2-Azabicyclo[2,2,1]-hept-5-ene-3-one is 39.3% and the optical purity is 98%.

* * * * *